(12) United States Patent
Watson et al.

(10) Patent No.: US 12,571,807 B2
(45) Date of Patent: Mar. 10, 2026

(54) REMOVABLE CASSETTE FOR AN IMAGING DEVICE

(71) Applicant: NEOGEN FOOD SAFETY US HOLDCO CORPORATION, Lansing, MI (US)

(72) Inventors: Hugh E. Watson, Prior Lake, MN (US); Thanh Q. Tran, Blaine, MN (US); Somanath M. Gadakar, Karnataka (IN); Vinod M. Rathod, Pune (IN)

(73) Assignee: NEOGEN FOOD SAFETY US HOLDCO CORPORATION, Lansing, MI (US)

( * ) Notice: Subject to any disclaimer, the term of this patent is extended or adjusted under 35 U.S.C. 154(b) by 541 days.

(21) Appl. No.: 17/904,851

(22) PCT Filed: Apr. 28, 2021

(86) PCT No.: PCT/IB2021/053510
§ 371 (c)(1),
(2) Date: Aug. 23, 2022

(87) PCT Pub. No.: WO2021/229343
PCT Pub. Date: Nov. 18, 2021

(65) Prior Publication Data
US 2023/0113428 A1 Apr. 13, 2023

(30) Foreign Application Priority Data
May 13, 2020 (IN) .............................. 202041020173

(51) Int. Cl.
| | |
|---|---|
| *C12M 1/00* | (2006.01) |
| *C12M 1/34* | (2006.01) |
| *G01N 35/00* | (2006.01) |

(52) U.S. Cl.
CPC ....... *G01N 35/00009* (2013.01); *C12M 31/10* (2013.01); *C12M 41/36* (2013.01);
(Continued)

(58) Field of Classification Search
CPC .................. C12M 31/10; C12M 41/36; G01N 2035/00019; G01N 2035/00306
See application file for complete search history.

(56) References Cited

U.S. PATENT DOCUMENTS

| | | | | | |
|---|---|---|---|---|---|
| 3,811,036 | A | * | 5/1974 | Perry | ..................... G06M 11/02 348/138 |
| 4,724,215 | A | * | 2/1988 | Farber | ................... G01N 35/00 348/82 |

(Continued)

FOREIGN PATENT DOCUMENTS

| | | |
|---|---|---|
| JP | 2022550896 A | 12/2022 |
| TW | 200921584 A | 5/2009 |

OTHER PUBLICATIONS

European Patent Office, JP 2022-550896 A, Patent Translate.
International Searching Authority, International Search Report, Jun. 25, 2021.

*Primary Examiner* — Jonathan M Hurst
(74) *Attorney, Agent, or Firm* — HYLTON-RODIC LAW PLLC

(57) ABSTRACT

The technology disclosed herein relates to, at least in part, a removable imaging cassette. An illumination plate is configured to transmit light. A cassette body defines an outer surface and a cassette cavity within the outer surface, where the outer surface surrounds the illumination plate. The cassette cavity abuts the illumination plate. A light source is disposed in the cassette cavity. Mating electrical contacts extend through the outer surface of the cassette body, where the mating electrical contacts are operably coupled to the light source.

21 Claims, 8 Drawing Sheets

(52) U.S. Cl.
CPC .............. *G01N 2035/00019* (2013.01); *G01N 2035/00306* (2013.01); *G01N 2333/195* (2013.01)

(56) References Cited

U.S. PATENT DOCUMENTS

| 5,448,652 | A | * | 9/1995 | Vaidyanathan | ........... | G06T 9/20 |
| | | | | | | 348/270 |
| 5,723,308 | A | * | 3/1998 | Mach | .................... | C12Q 1/045 |
| | | | | | | 435/243 |
| 6,002,789 | A | * | 12/1999 | Olsztyn | .................. | C12M 41/36 |
| | | | | | | 382/173 |
| 6,271,022 | B1 | * | 8/2001 | Bochner | .............. | G01N 35/028 |
| | | | | | | 422/65 |
| 8,417,013 | B2 | * | 4/2013 | Bolea | .................... | C12Q 1/045 |
| | | | | | | 382/133 |
| 8,759,080 | B2 | * | 6/2014 | Graessle | ........... | G01N 15/1433 |
| | | | | | | 422/63 |
| D742,767 | S | * | 11/2015 | Saga | ........................... | D24/216 |
| 9,968,315 | B2 | | 5/2018 | Ogura et al. | | |
| 10,495,563 | B1 | | 12/2019 | Skiffington et al. | | |
| 10,563,164 | B1 | * | 2/2020 | Skiffington | ............. | C12Q 1/06 |
| 11,867,707 | B1 | * | 1/2024 | Bertrand | ........... | G01N 35/1081 |
| 2004/0101952 | A1 | | 5/2004 | Vent | | |
| 2005/0053265 | A1 | * | 3/2005 | Graessle | ............... | C12M 41/36 |
| | | | | | | 382/128 |
| 2006/0166305 | A1 | * | 7/2006 | Jiang | ................... | G01N 21/253 |
| | | | | | | 435/29 |
| 2006/0194193 | A1 | * | 8/2006 | Tsuruta | ................. | C12M 41/36 |
| | | | | | | 435/287.1 |
| 2019/0178856 | A1 | * | 6/2019 | Freitag | .................. | G01N 30/74 |

* cited by examiner

REMOVABLE CASSETTE FOR AN IMAGING DEVICE

CROSS REFERENCE TO RELATED APPLICATIONS

This application is a national stage filing under 35 U.S.C. 371 of PCT/IB2021/053510, filed Apr. 28, 2021, which claims priority to Indian Provisional Application No. 202041020173, filed May 13, 2020, the disclosure of which is incorporated by reference in its/their entirety herein.

TECHNOLOGICAL FIELD

The present disclosure is generally related to an imaging device. More particularly, the present disclosure is related to a removable cassette for an imaging device.

BACKGROUND

Testing for biological contamination in foods or other materials has become an important and often mandatory requirement for developers and distributors of food products. Biological testing is also used to identify bacteria or other agents in laboratory samples such as blood samples taken from medical patients, laboratory samples developed for experimental purposes, and other types of biological samples. Various techniques and devices can be used to improve biological testing and to streamline and standardize the biological testing process.

Biological growth plates can be used to enumerate or identify the presence of bacteria so that corrective measures can be performed (in the case of food testing) or proper diagnosis can be made (in the case of medical use). In other applications, biological growth plates may be used to rapidly grow bacteria or other biological agents in laboratory samples, e.g., for experimental purposes.

A wide variety of biological growth plates have been developed. As one example, biological growth plates have been developed by 3M Company (hereafter "3M") of St. Paul, Minn. Biological growth plates are sold by 3M under the trade name PETRIFILM plates. Biological growth plates can be utilized to facilitate the rapid growth and detection of bacteria or other biological agents commonly associated with food contamination, including, for example, aerobic bacteria, *E. coli*, coliform, enterobacteriaceae, yeast, mold, *Staphylococcus aureus*, Listeria, Campylobacter, and the like. The use of PETRIFILM plates, or other growth media, can simplify bacterial testing of food samples.

In examples, a food sample or laboratory sample can be placed on a biological growth plate, and then the plate can be inserted into an incubation chamber. Typically, after incubation, the biological growth plate is manually read by a technician who is trained to identify the bacteria or other biological agents on the growth plate. An imaging device can also be used to scan or count bacterial colonies, or the amount of a particular biological agent on a biological growth plate. After incubation, the biological growth plate can be placed into the imaging device for automated detection and enumeration of bacterial growth. The imaging device can automate the detection and enumeration of bacteria or other biological agents on a biological growth plate, and thereby improve the biological testing process by reducing human error.

In various industries imaging devices are used extensively, and each imaging device can be used to examine numerous biological growth plates per day. The biological growth plates can carry contaminants such as dust, which may imbed on the imaging device, such as on the feed mechanisms that drive the biological growth plates through the device or around the mounting surface that receives the biological growth plate. A build-up of dust and other contaminants may impede proper operation of the device and may even create biohazardous conditions. Furthermore, cleaning of the imaging device, which is usually done manually, can be challenging because some components may be difficult to access. Cleaning and other maintenance operations may also pose a risk to electrical components.

SUMMARY

The technology disclosed herein generally relates to an imaging device that has a removable cassette. The removable cassette can be powered when installed in the main body. Removing the cassette from the main body may disconnect the cassette from the power source, which may be advantageous for performance of maintenance on the cassette, such as cleaning. Furthermore, the cassette may define a feed mechanism that receives samples on biological growth plates. By having a cassette that is removable from the main body, surfaces defined by the feed mechanism may advantageously be more easily accessed by a user for maintenance compared to existing imaging devices.

Some embodiments relate to a removable imaging cassette. The removable imaging cassette has an illumination plate that is configured to transmit light. A cassette body defines an outer surface. The outer surface surrounds the illumination plate. A cassette cavity is within the outer surface. The cassette cavity abuts the illumination plate. A light source is disposed in the cassette cavity. Mating electrical contacts extend through the outer surface of the cassette body. The mating electrical contacts are operably coupled to the light source.

In some such embodiments, a drive wheel is rotatably coupled to the outer surface of the cassette body adjacent the illumination plate. A motor is operably coupled to the drive wheel. The motor is disposed in the cassette cavity. The mating electrical contacts is operably coupled to the motor. Additionally or alternatively, a manual rotary knob is operably coupled to the drive wheel. Additionally or alternatively, the removable imaging cassette has a plate clamp coupled to the cassette body and a roller wheel rotatably coupled to the plate clamp, where the roller wheel is configured to align with the drive wheel. Additionally or alternatively, the plate clamp is pivotably coupled to the outer surface of the cassette body. Additionally or alternatively, a manually engageable handle is coupled to the cassette body. Additionally or alternatively, the cassette body defines a media slot extending from the outer surface to the illumination plate. Additionally or alternatively, the cassette cavity is isolated from an ambient environment.

Some embodiments disclosed herein relate to an imaging device. The imaging device has a main body having an outer shell. The main body defines a main cavity. The main body defines a cassette receptacle extending through the outer shell to the main cavity. Source electrical contacts are coupled to the outer shell, where the source electrical contacts are exposed in the main cavity. A power supply connector is configured to couple to a power source. The power supply connector is in electrical communication with the source electrical contacts. The imaging device has an imaging cassette removably installed in the cassette receptacle. The imaging cassette has an illumination plate configured to transmit light. The imaging cassette has a cassette body defining an outer surface and a cassette cavity within the outer surface. The outer surface surrounds the illumination plate. The cassette cavity abuts the illumination plate. The imaging cassette has mating electrical contacts that are configured to (1) electrically mate with the source electrical contacts when the imaging cassette is installed in the cassette receptacle, and (2) electrically disconnect from the source electrical contacts when the imaging cassette is removed from the cassette receptacle.

In some such embodiments, the illumination plate is configured to receive a biological growth plate. Additionally or alternatively, a light source is disposed in the cassette cavity, where the mating electrical contacts are operably coupled to the light source. Additionally or alternatively, the imaging device has a transparent barrier mounted to the main body in the main cavity between the cassette receptacle and an imaging cavity. Additionally or alternatively, the imaging device has a pairing confirmation assembly having a reader and an identifier. The reader is configured to read the identifier, and the pairing confirmation assembly is configured to compare the identifier to stored configuration data.

Additionally or alternatively, the main body has a user interface in data communication with the reader, where the user interface is configured to notify a user that the identifier does not match the stored configuration data. Additionally or alternatively, the imaging cassette has a drive wheel rotatably coupled to the cassette body adjacent the illumination plate, and a motor operably coupled to the drive wheel. The motor is disposed in the cassette cavity and the mating electrical contacts are operably coupled to the motor. Additionally or alternatively, a manual rotary knob is operably coupled to the drive wheel.

Additionally or alternatively, a plate clamp is coupled to the cassette body and a roller wheel is rotatably coupled to the plate clamp, where the roller wheel is configured to align with the drive wheel. Additionally or alternatively, the plate clamp is pivotably coupled to the outer surface of the cassette body. Additionally or alternatively, the imaging device has a manually engageable handle coupled to the cassette body. Additionally or alternatively, the cassette body defines a media slot extending from the outer surface to the illumination plate. Additionally or alternatively, the cassette cavity is isolated from an ambient environment.

The above summary is not intended to describe each embodiment or every implementation. Rather, a more complete understanding of illustrative embodiments will become apparent and appreciated by reference to the following Detailed Description of Exemplary Embodiments and claims in view of the accompanying figures of the drawing.

BRIEF DESCRIPTION OF THE DRAWINGS

The present technology may be more completely understood and appreciated in consideration of the following detailed description of various embodiments in connection with the accompanying drawings.

The figures are rendered primarily for clarity and, as a result, are not necessarily drawn to scale. Moreover, various structure/components, including but not limited to fasteners, electrical components (wiring, cables, etc.), and the like, may be shown diagrammatically or removed from some or all of the views to better illustrate aspects of the depicted embodiments, or where inclusion of such structure/components is not necessary to an understanding of the various exemplary embodiments described herein. The lack of illustration/description of such structure/components in a particular figure is, however, not to be interpreted as limiting the scope of the various embodiments in any way.

DETAILED DESCRIPTION

The technology disclosed herein generally relates to an imaging device that has a removable cassette. The removable cassette can be powered when installed in the main body. Removing the cassette from the main body may disconnect the cassette from the power source, which may be advantageous for performance of maintenance on the cassette, such as cleaning. Furthermore, the cassette may define a feed mechanism that receives samples on biological growth plates. By having a cassette that is removable from the main body, surfaces defined by the feed mechanism may advantageously be more easily accessed by a user for maintenance compared to existing imaging devices.

Figure 1:
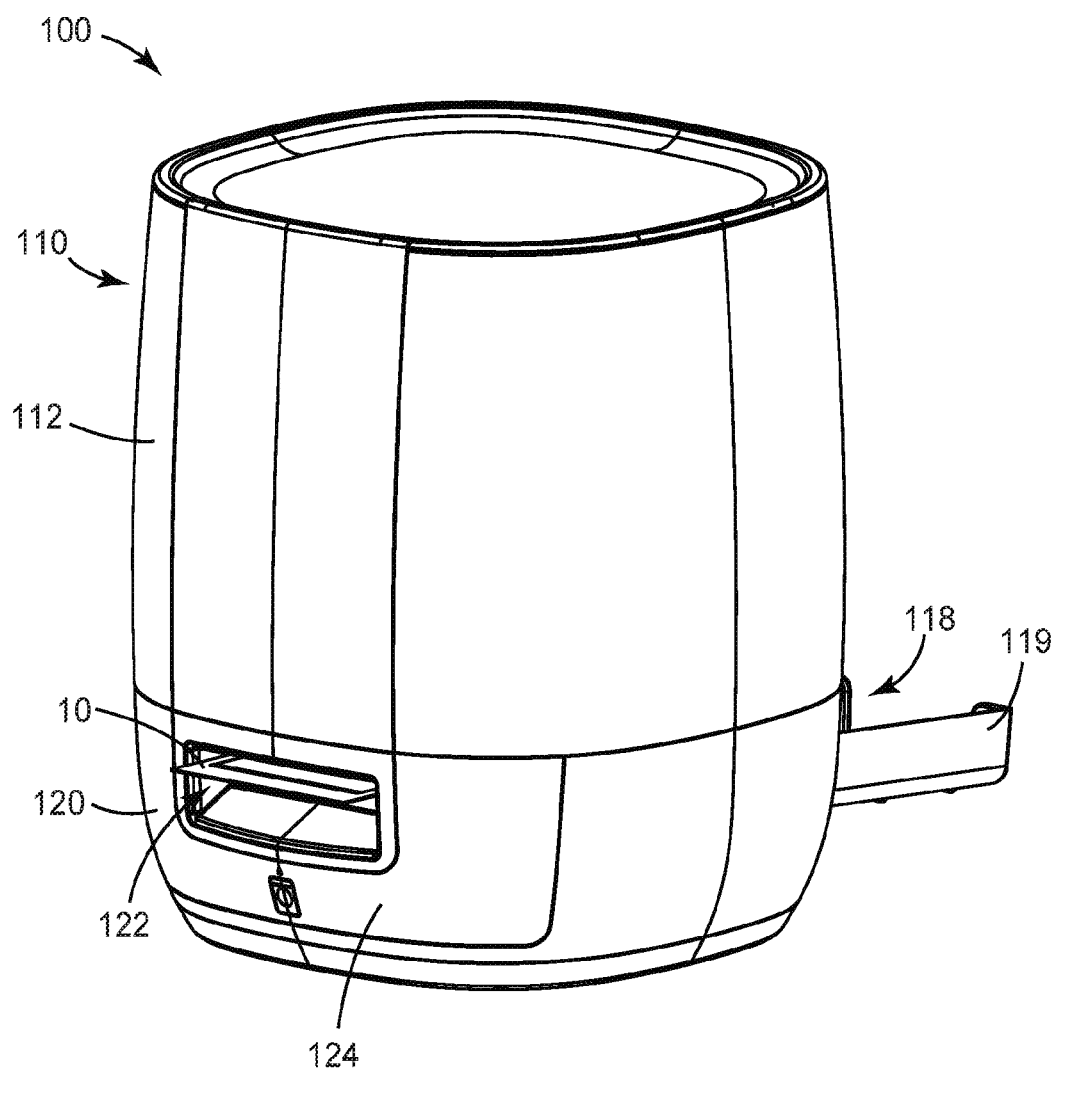
FIG. 1 is a perspective view of an example system consistent with the technology disclosed here.
Figure 2:
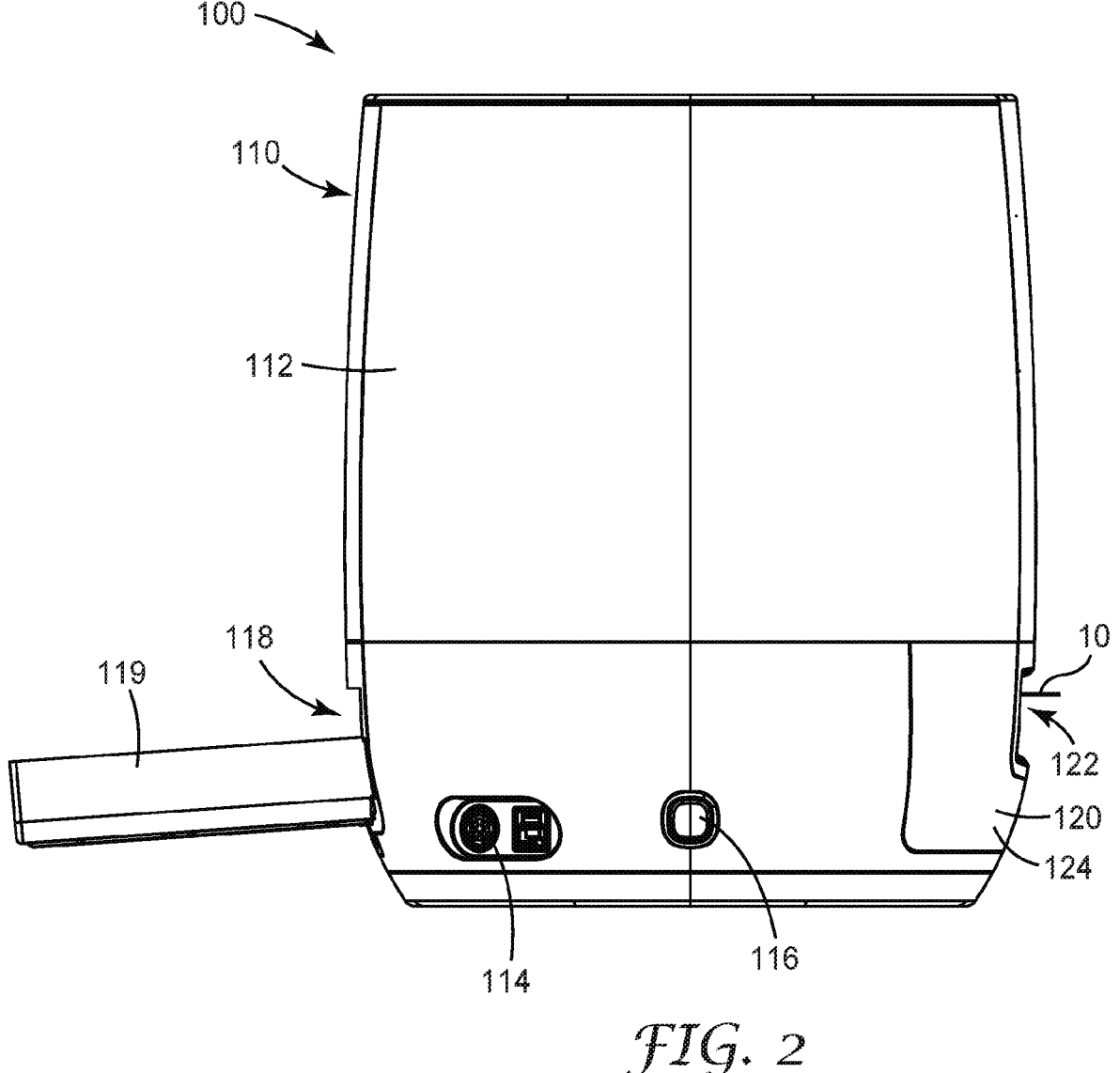
FIG. 2 is a side view of an example system consistent with FIG. 1.

FIG. 1 depicts an example imaging device 100 consistent with various embodiments, and FIG. 2 depicts an example side view of the imaging device 100. The imaging device 100 is generally configured to receive and scan a biological growth plate 10. The imaging device 100 defines a feed inlet 122 that is configured to receive the biological growth plate 10. The imaging device 100 defines a feed outlet 118 that is configured to release the biological growth plate 10. In various embodiments, the imaging device 100 automatically feeds the biological growth plate 10 from the feed inlet 122 to the feed outlet 118, examples of which will be described in detail below.

The imaging device 100 has a main body 110 and an imaging cassette 120. The imaging cassette 120 is generally configured to receive the biological growth plate 10. The main body 110 is configured to removably receive the imaging cassette 120. In various embodiments the main body 110 can have a manually or electrically engageable release mechanism 116 that is configured to detach the imaging cassette 120 from the main body 110. In some embodiments the release mechanism 116 is configured to discharge the imaging cassette 120 from the main body 110. In the current example, the release mechanism 116 is a manually depressible button.

The main body 110 has an outer shell 112. The outer shell 112 is configured to house system components. The outer shell 112 can be configured to isolate system components contained therein from the ambient environment, where "isolate" is defined herein as creating a physical barrier to prevent the ingress of debris.

In various embodiments, the main body 110 is configured to couple to a power source, such as alternating current (AC) or direct current (DC) power source. In some embodiments, the main body 110 can house the power source, such as where the power source is a battery. In some embodiments, the main body is configured to electrically couple to an external power source, such as an electrical outlet. In various embodiments, the main body 110 has a power supply connector 114 (FIG. 2) that is configured to electrically connect with the power source such as a battery or an electrical outlet.

In various embodiments, the main body 110 is configured to distribute power from the power supply connector 114 (and the power source) to energize system components. In various embodiments, the main body 110 is configured to distribute power from the power source to energize system components of the main body 110 and the imaging cassette 120. The main body 110 can be configured to energize system components of the imaging cassette 120 when the imaging cassette 120 is installed in the main body 110.

The main body 110 is generally configured to scan the biological growth plate 10. Each of the main body 110 and the imaging cassette 120 can be configured to illuminate the biological growth plate 10. Such functionality will be described in more detail below.

The current example imaging device 100 has an optional outlet tray 119 that is configured to receive the biological growth plate 10 after having been fed through the feed outlet 118. The outlet tray 119 extends outward from the main body 110. The outlet tray 119 is positioned vertically below the feed outlet 118 so that gravity directs a biological growth plate 10 onto the outlet tray 119 after being discharged from the main body 110 through the feed outlet 118.

Figure 3:
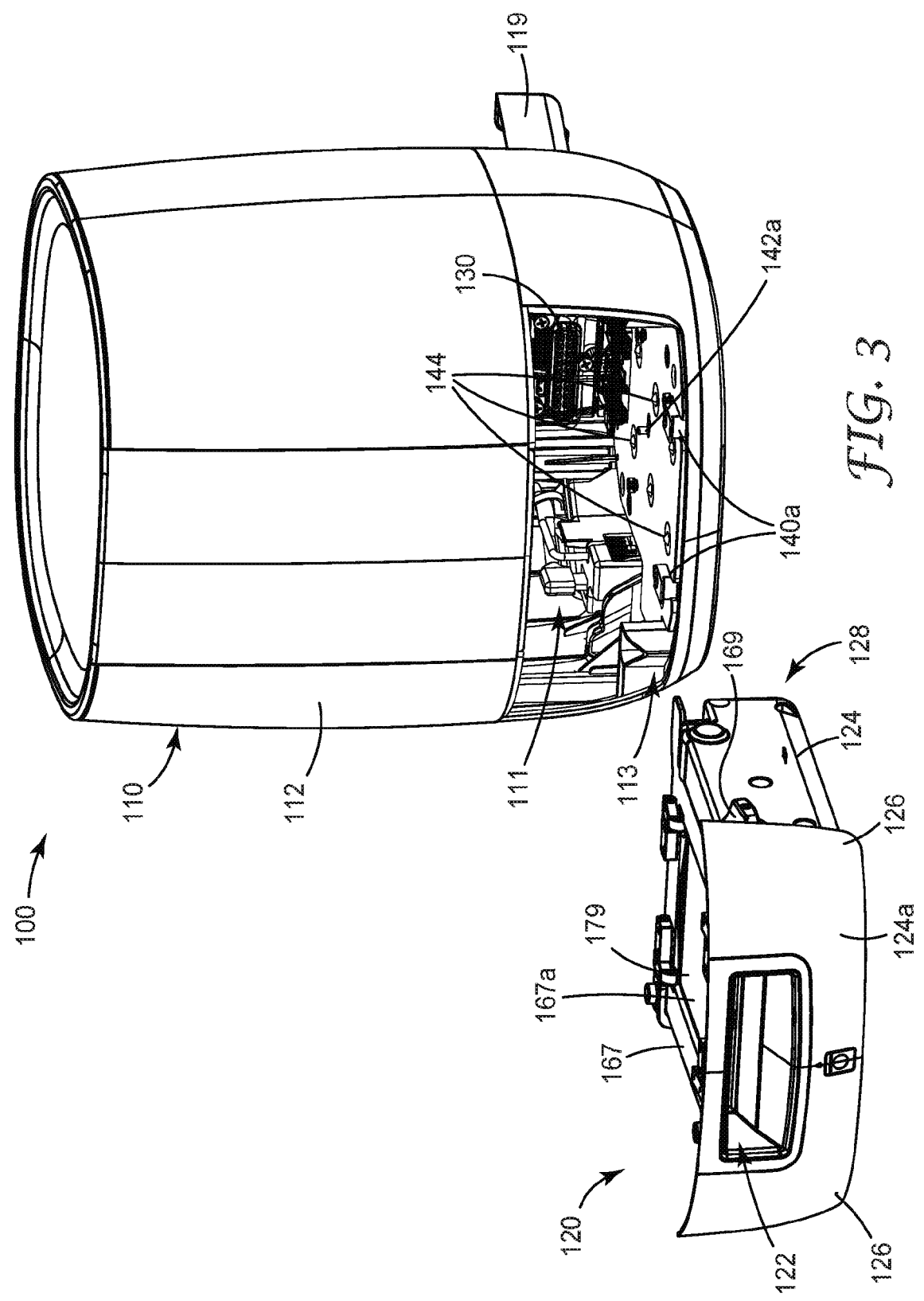
FIG. 3 is an exploded view of an example system consistent with FIG. 1.

FIG. 3 depicts an example exploded view consistent with an imaging device 100 of FIGS. 1 and 2. In the current view, the imaging cassette 120 is depicted exploded from the main body 110. From this view a main cavity 111 that is defined by the main body 110 is visible. The main cavity 111 is generally configured to receive system components. The main cavity 111 is generally isolated from the ambient environment.

The main body 110 defines a cassette receptacle 113 that extends through the outer shell 112 to the main cavity 111. The imaging cassette 120 is configured to be removably installed in the cassette receptacle 113. The main body 110 has source electrical contacts 130 that are exposed in the cassette receptacle 113 of the main cavity 111. The source electrical contacts 130 are in electrical communication with the power supply connector 114 (FIG. 2). The source electrical contacts 130 are configured to supply power to the imaging cassette 120 when the imaging cassette 120 is installed in the main body 110. The source electrical contacts 130 are configured to electrically disconnect from the imaging cassette 120 while maintaining power to the main body 110. The source electrical contacts 130 are configured to electrically disconnect from the imaging cassette 120 without removing power to the main body 110. In various embodiments the source electrical contacts 130 are coupled to the outer shell 112, but not necessarily directly coupled to the outer shell 112. The source electrical contacts 130 can have a fixed position relative to the main body 110.

The imaging cassette 120 is generally configured to be installed and removed from the cassette receptacle 113 of the main body 110. In particular, the imaging cassette 120 has a cassette body 124 defining an outer surface of the imaging cassette 120 that is configured to be received by the cassette receptacle 113. In the current example, a substantial portion of the cassette body 124 is received by the cassette receptacle 113. However, a facing surface 124a of the cassette body 124 is not received by the cassette receptacle 113. The facing surface 124a of the cassette body 124 extends across the outer shell 112 over the cassette receptacle 113. As such, the facing surface 124a of the cassette body 124 defines an outer surface of the imaging device 100.

Figure 4:
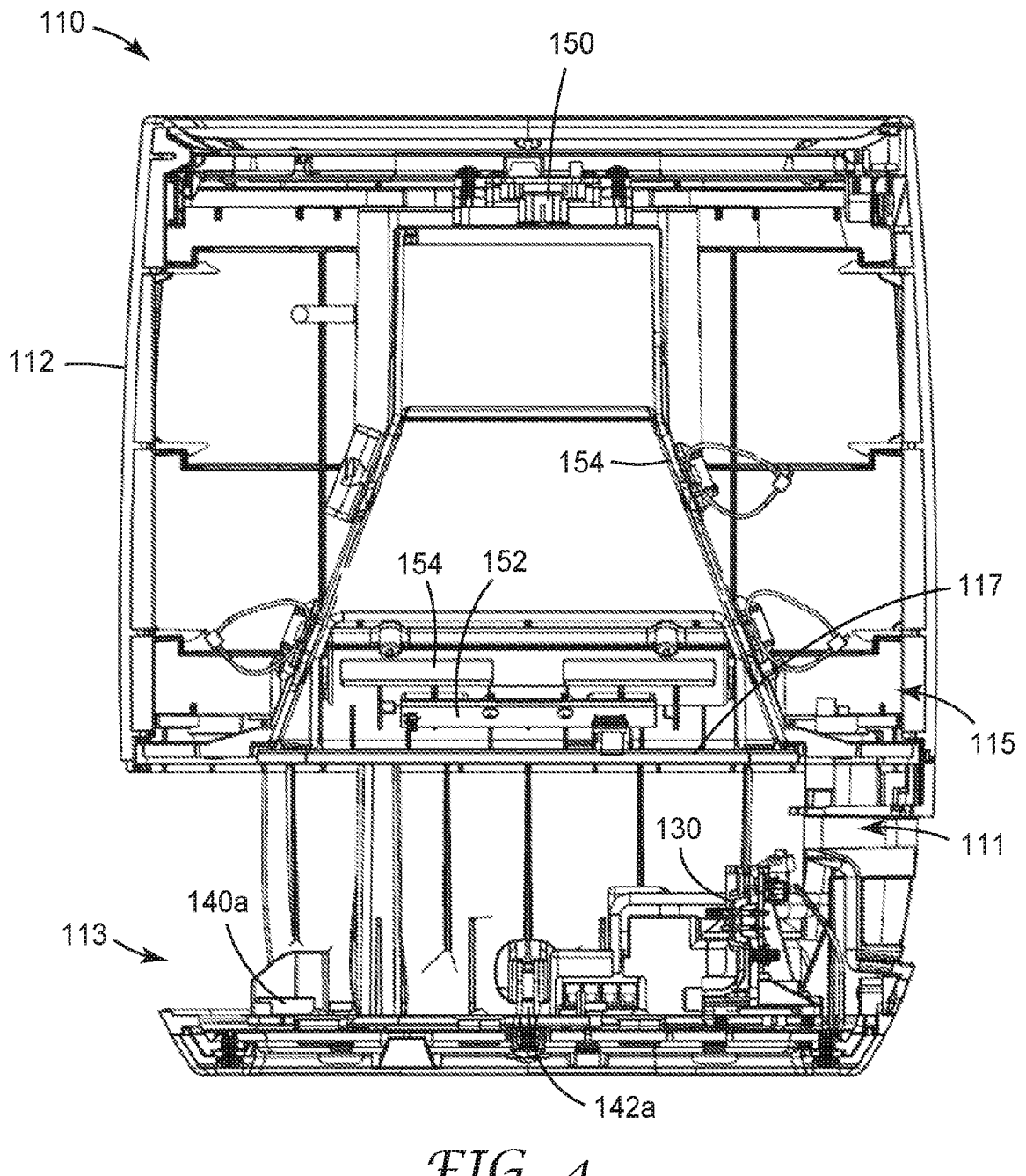
FIG. 4 is a cross-sectional view of an example main body, consistent with various embodiments.
Figure 5:
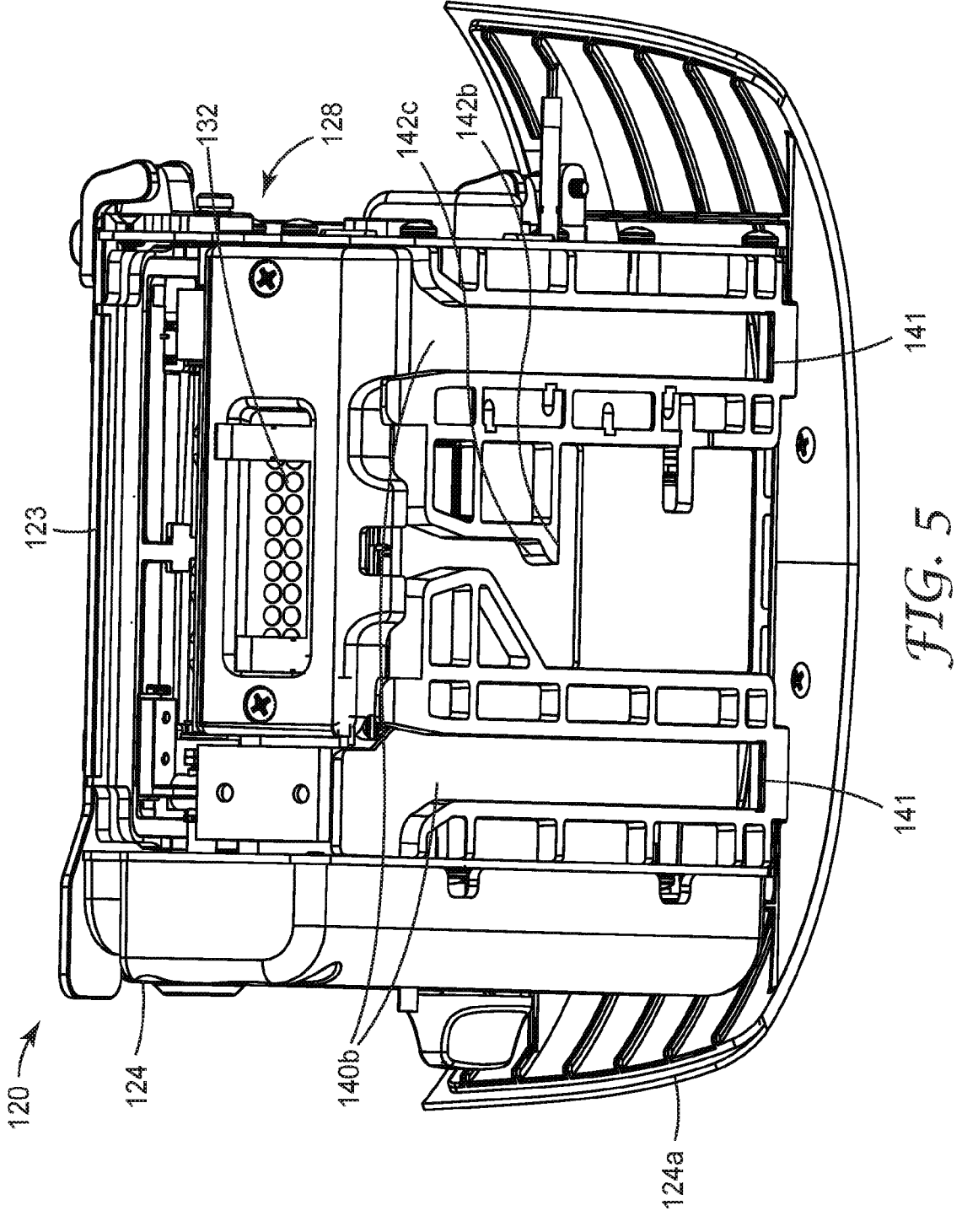
FIG. 5 is a first perspective view of an example cassette.

The imaging device 100 can have a variety of features to facilitate installation and removal of the imaging cassette 120 relative to the main body 110. FIG. 3 can be viewed in conjunction with FIG. 4 (a cross-sectional view of the main body) and FIG. 5 (a perspective view of the imaging cassette 120) for visibility of components discussed herein. Mating alignment features 140a (FIGS. 3-4), 140b (FIG. 5) can be mutually defined by the main body 110 and imaging cassette 120. The mating alignment features 140a, 140b are configured to align the imaging cassette 120 within the cassette receptacle 113. In the example of FIG. 3, the mating alignment features include alignment tabs 140a of the main body 110. The alignment tabs 140a extend into the cassette receptacle 113 from the outer shell 112. The mating alignment features 140a, 140b include slide channels 140b of the imaging cassette 120 that are configured to slidably receive the alignment tabs 140a. The slide channels 140b are defined from an insertion end 128 of the imaging cassette 120 towards the opposite end of the imaging cassette 120. In some embodiments the main body can define a slide channel and the imaging cassette can define tabs that are configured to be slidably received by the slide channels. Alternate alignment features are also contemplated.

The main body 110 and the cassette body 124 can be configured to mutually engage to secure the cassette body 124 to the main body 110 upon installation. In various embodiments the alignment tabs 140a can be configured to secure the cassette body 124 to the main body 110. The alignment tabs 140a can be configured to frictionally engage the cassette body 124 at a terminal end 141 of the slide channels 140b. The main body 110 and the cassette body 124 can have additional and alternate engagement features to secure the cassette body 124 to the main body 110 upon installation.

The imaging device 100 can have features that reduce friction between the imaging cassette 120 and the main body 110. In the example visible in FIG. 3, roller balls 144 are disposed between the main body 110 and the imaging cassette 120 within the cassette receptacle 113. The roller balls 144 are configured to facilitate installation and removal of the imaging cassette 120 in the main body 110. Additional or alternately-positioned roller balls can also be disposed between the imaging cassette 120 and the main body. Other approaches can also be used to reduce friction between the imaging cassette 120 in the main body 110.

The imaging device 100 can have a latching mechanism 142a (FIGS. 3-4), 142b (FIG. 5) that is configured to secure the imaging cassette 120 in the cassette receptacle 113. The latching mechanism 142a, 142b can be configured to secure the position of the imaging cassette 120 within the cassette receptacle 113. The latching mechanism 142a, 142b can be configured to prevent the unintended removal of the imaging cassette 120 from the cassette receptacle 113. The latching mechanism 142a, 142b can be configured to physically obstruct removal of the imaging cassette 120 from the cassette receptacle 113. Various types of latching mechanisms can be employed.

In this example, the latching mechanism 142a, 142b is an engagement pin 142a of the main body 110 that extends into the cassette receptacle 113 and an engagement structure 142b of the imaging cassette 120 that mechanically engages the engagement pin 142a upon installation of the imaging cassette 120 in the cassette receptacle 113. The engagement pin 142a is biased into a first position, and, as the imaging cassette 120 is inserted in the cassette receptacle 113 a ramped surface 142*c* of the imaging cassette 120 translates the engagement pin 142*a* out of the first position to accommodate installation of the imaging cassette 120. Once the imaging cassette 120 is in an installed position, the ramped surface 142*c* ends, and the engagement pin 142*a* returns to its biased position, which mechanically engages the engagement structure 142*b* to obstruct removal of the imaging cassette 120 from the cassette receptacle 113.

In various embodiments, the latching mechanism 142*a*, 142*b* is in operative communication with the release mechanism 116 (FIG. 2). In the current example, to remove the imaging cassette 120, the release mechanism 116 can be deployed to translate the engagement pin 142*a* out of engagement with the engagement structure 142*b*. Other types of latching mechanisms can be used to form a latched connection between the imaging cassette 120 and the main body 110.

In some embodiments, a biasing member such as a compression spring is disposed between the imaging cassette 120 and the cassette receptacle 113. The biasing member is configured to bias the imaging cassette 120 outside of a fully installed position in the cassette receptacle 113. In such embodiments, installing the imaging cassette 120 in the cassette receptacle 113 requires manually overcoming the force of the biasing member to engage the latching mechanism 142*a*, 142*b*. Upon deploying the release mechanism 116, the biasing member partially ejects the imaging cassette 120 from the cassette receptacle 113. Grasping regions 126 defined along the facing surface 124*a* of the imaging cassette 120 separate from the outer shell 112, allowing the user to manually grasp the imaging cassette 120 to complete removal of the imaging cassette 120 relative to the main body 110. The grasping regions 126 can also be grasped by a user to install the imaging cassette 120 in the main body 110. In some embodiments the grasping region can be a separate handle that is attached to or integral with the cassette body.

The imaging cassette 120 is configured to be electrically mated with the source electrical contacts 130 of the main body 110 upon installation in the cassette receptacle 113. In particular, referring to FIG. 5, the imaging cassette 120 has mating electrical contacts 132 that are configured to electrically mate with the source electrical contacts 130 when the imaging cassette 120 is installed in the cassette receptacle 113. The mating electrical contacts 132 can be configured to mechanically mate with the source electrical contacts 130 when the imaging cassette 120 is installed in the cassette receptacle 113. The mating electrical contacts 132 are configured to electrically disconnect from the source electrical contacts 130 when the imaging cassette 120 is removed from the cassette receptacle 113. In various embodiments the mating electrical contacts 132 are configured to mechanically disconnect from the source electrical contacts 130 when the imaging cassette 120 is removed from the cassette receptacle 113.

In various embodiments, the imaging cassette 120 has electrical components that are energized upon installation in the cassette receptacle 113, when the mating electrical contacts 132 are in electrical communication with the source electrical contacts 130. Such electrical components are correspondingly de-energized upon removal of the imaging cassette 120 from the cassette receptacle 113. Such a configuration may advantageously reduce the risk of electrical shock while performing maintenance operations on the cassette receptacle. Such a configuration may advantageously reduce the risk of electrically damaging the system when applying fluids such as a cleaning solution to the imaging cassette 120. Such a configuration advantageously allows maintenance of the imaging cassette 120 without rebooting the main body 110.

Figure 7:
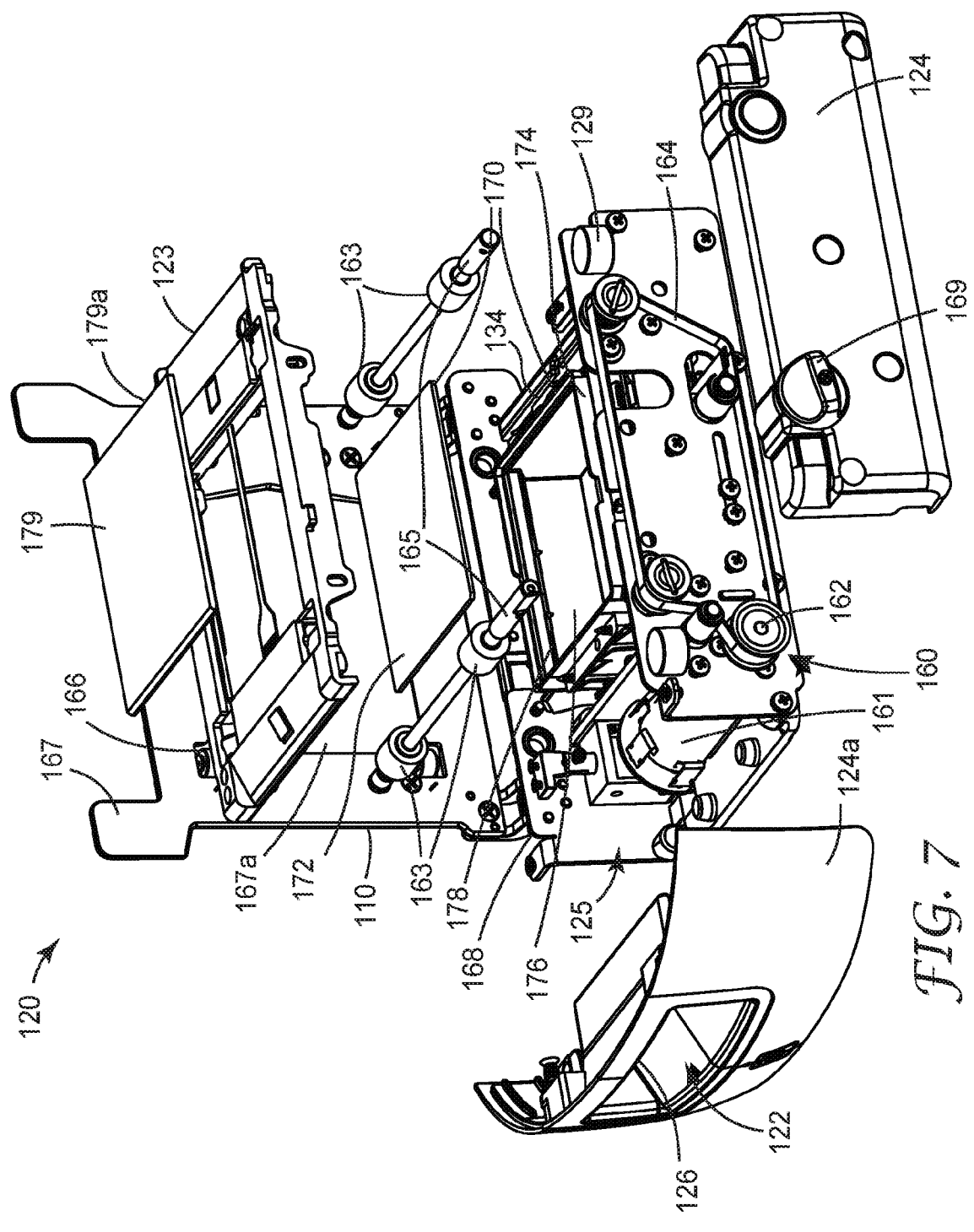
FIG. 7 is an exploded view of an example cassette consistent with FIG. 5.

In various embodiments electrical communication between the imaging cassette 120 and the cassette receptacle 113 is dictated by a hot swap controller 134 (an example location of which is represented in FIG. 7). The hot swap controller 134 can facilitate removal of the imaging cassette 120 from the cassette receptacle 113 without cutting off the power to the main body 110. The hot swap controller 134 can be configured to limit surge currents or back electromagnetic field (EMF) effects caused by removal of power. The hot swap controller 134 can facilitate installation of the imaging cassette 120 in the cassette receptacle 113. Upon installing the imaging cassette 120 in the cassette receptacle 113, the hot swap controller 134 can be configured to slow the rise of the voltage applied to the cassette so that a sudden rise in the voltage doesn't cause a damaging in-rush of current or back EMF effects. The hot swap controller 134 can be configured to monitor the voltage applied across the mating electrical contacts 132 by the source electrical contacts 130. The hot swap controller 134 can allow a voltage to be applied to the circuitry of the imaging cassette 120 via the mating electrical contacts 132 when the monitored current is stable. The hot swap controller 134 can be configured to withhold control signals from the imaging cassette until the voltage is stable. In some embodiments the hot swap controller 134 is coupled to the imaging cassette 120. In various embodiments, the hot swap controller 134 is coupled to the mating electrical contacts 132.

The main body 110 can house various imaging components, processing components, electrical components, and the like. As best visible in FIG. 4, the main body 110 can have an image capture device 150 such as a camera or scanner, various light sources 152, reflector surfaces 154, and the like. While not currently visible, the main body 110 can also have various processors, data cables, electrical cables, and the like. In various embodiments, the main cavity 111 of the main body 110 can be separated into a cassette receptacle 113 and an imaging cavity 115 by a barrier 117. The imaging cavity 115 can be configured to contain various imaging and processing components. In various embodiments the barrier 117 is generally transparent to facilitate imaging operations. The barrier 117 can be mounted to the main body 110. The outer shell 112 and the barrier 117 are generally configured to isolate the imaging cavity from the ambient environment. The barrier 117 and the outer shell 112 can isolate various imaging and processing components to limit interference with those components during maintenance operations.

Figure 6:
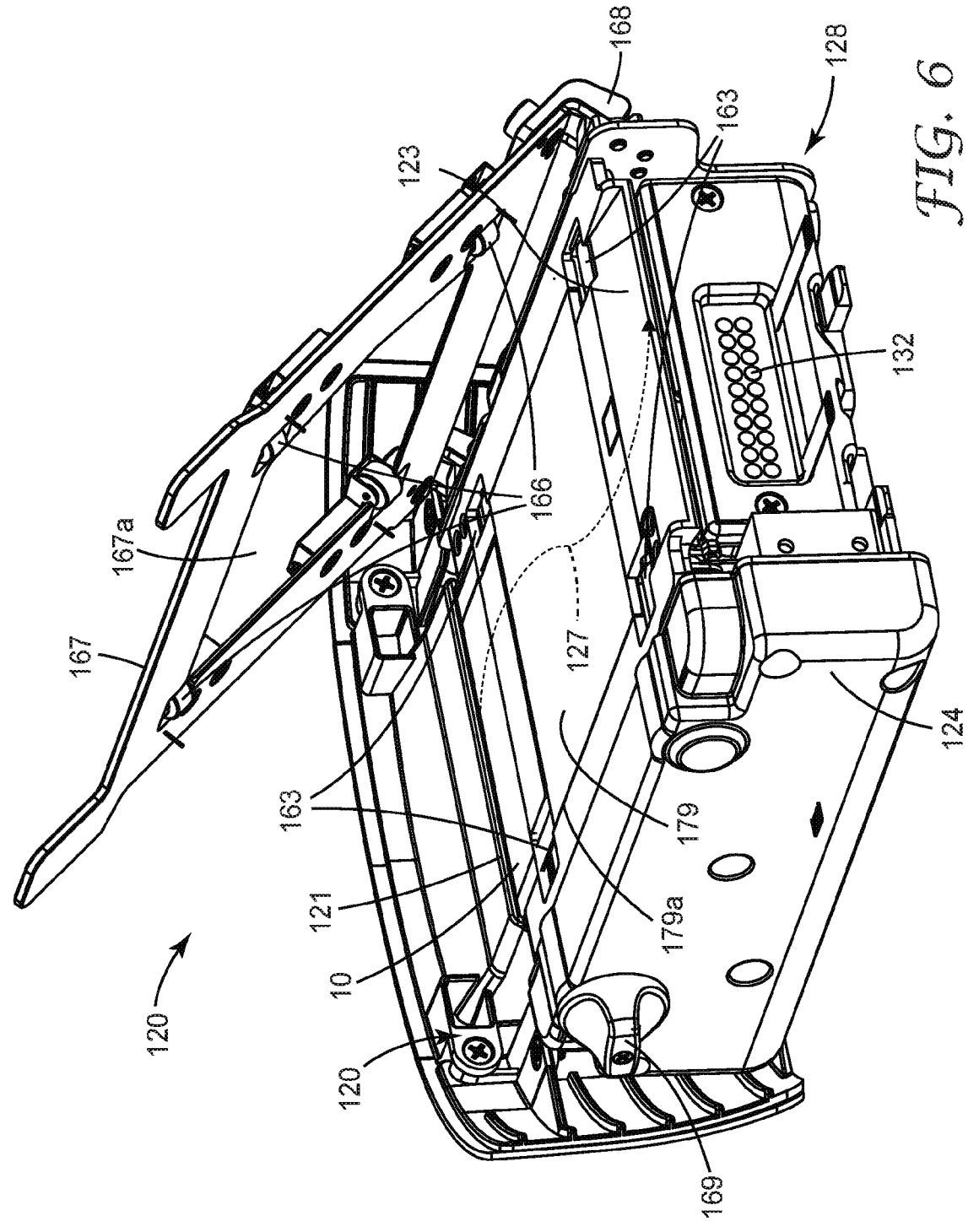
FIG. 6 is a second perspective view of an example cassette consistent with FIG. 5.

FIG. 6 depicts a perspective view of the imaging cassette 120 consistent with embodiments, where the imaging cassette 120 partially receives a biological growth plate 10. FIG. 7 depicts an exploded view of the imaging cassette 120. These figures can be viewed in combination with FIGS. 3 and 5 for a further understanding of the imaging cassette 120. The imaging cassette 120 is generally configured to house various system components of the imaging device 100. The imaging cassette 120 can be configured to isolate various system components from the ambient environment. The imaging cassette 120 is generally configured to feed the biological growth plate 10 through the imaging device 100 for execution of imaging operations. In various embodiments the imaging cassette 120 is configured to illuminate the biological growth plate 10 for imaging operations by the imaging device 100.

As discussed above, the imaging cassette 120 defines a cassette cavity 125 within the outer surface. The cassette cavity 125 is configured to house system components. In various embodiments the cassette cavity 125 is isolated from the ambient environment.

The imaging cassette 120 has an illumination plate 179 that is generally configured to transmit light. The illumination plate 179 is generally transparent and can be constructed of glass, plastic, crystal, and the like. In embodiments, light generated in the cassette cavity 125 of the imaging cassette 120 is transmitted through the illumination plate 179. The illumination plate 179 generally abuts the cassette cavity 125. In some embodiments, light from the main body 110 is transmitted through the illumination plate 179 to the biological growth plate 10. The illumination plate 179 is generally configured to receive the biological growth plate 10 (FIG. 6). In some embodiments, the illumination plate 179 forms a hollow channel through which the biological growth plate 10 passes. In some embodiments, the illumination plate 179 is a layer that the biological growth plate 10 abuts. More specifically, the biological growth plate 10 can be received over a surface of the illumination plate 179. The biological growth plate 10 is configured to extend across a substantial portion of the illumination plate 179.

As discussed above, the imaging cassette 120 has a cassette body 124 that defines an outer surface of the imaging cassette 120. In various embodiments, the illumination plate 179 defines a portion of the outer surface of the imaging cassette 120. In such embodiments, the outer surface defined by the cassette body 124 surrounds the illumination plate 179.

A light source 170 can be disposed in the cassette cavity 125 of the imaging cassette 120 that is configured to generate and transmit light. The light source 170 can be configured to transmit light through the illumination plate 179. The mating electrical contacts 132 (FIGS. 5 and 6) are operably coupled to the light source 170. As such, when the imaging cassette 120 is installed in the main body 110 such that the mating electrical contacts 132 and the source electrical contacts 130 are in electrical communication, the light source 170 can be energized by the power supply connector 114.

The light source 170 has an emitter face 172 that is configured to emit light to the illumination plate 179. The material forming the emitter face 172 can be transparent or translucent. The emitter face 172 can be constructed of glass, plastic, crystal, or other materials. The emitter face 172 can be parallel to the illumination plate 179, in some embodiments. In some embodiments, the emitter face 172 abuts the illumination plate 179, where "abuts" is intended to mean that the emitter face 172 and the illumination plate 179 are touching. In some embodiments, the emitter face 172 and the illumination plate 179 are adjacent, with a spacing region defined between them. In some embodiments, the emitter face of the light source can be defined by a light generation device itself, such as a light emitting diode (LED) or other device.

In the current example, the light source 170 is an illumination box 174 defining an illumination cavity 176. The emitter face 172 is coupled to the illumination box 174. The emitter face 172 extends across the illumination cavity 176. A light generation device 178 is disposed in the illumination cavity 176. The light generation device 178 is configured to emit light in the illumination cavity 176. The light can be reflected off of various inner surfaces of the illumination box 174. The light can be transmitted through the emitter face 172 towards the illumination plate 179. In this specific example, the light generation device 178 is operably coupled to the mating electrical contacts 132.

The imaging cassette 120 defines the feed inlet 122 through the cassette body 124 that is configured to receive the biological growth plate 10. In this particular example, the cassette body 124 defines a media slot 121 extending from the outer surface of the cassette body 124 to the illumination plate 179. The imaging cassette 120 has a feed system that is configured to feed the biological growth plate 10 through the imaging device 100. The feed system can be configured to advance the biological growth plate 10 from the feed inlet 122 to the feed outlet 118 (FIG. 2) via the illumination plate 179. The feed system can be configured to advance the biological growth plate 10 from the feed inlet 122 to a cassette feed outlet 123 via the illumination plate 179. The imaging cassette 120 can define a feed channel 127 that defines the translation pathway of the biological growth plate 10 from the feed inlet 122 to the cassette feed outlet 123.

The feed system can have a drive assembly 160 that is configured to frictionally engage the biological growth plate 10 to linearly translate the biological growth plate 10 through the imaging device 100. The drive assembly 160 has a motor 161 disposed in the cassette cavity 125. The mating electrical contacts 132 are in operable communication with the motor 161. The motor 161 is in electrical communication with the mating electrical contacts 132.

In this particular example, at least one drive wheel 163 is configured to frictionally engage the biological growth plate 10. Each of the drive wheels 163 are configured to frictionally engage the biological growth plate 10. In various embodiments, the drive wheels 163 are configured to engage edge regions of the biological growth plate 10 to prevent interaction with a central region of the biological growth plate. The central region of the biological growth plate can be an inoculation area that is generally used for bacterial growth and then imaging. The drive wheels 163 are rotatably coupled to the cassette body 124 adjacent the illumination plate 179. The motor 161 has an output shaft 162 that is operably coupled to each of the drive wheels 163. In particular, the output shaft 162 is rotatably coupled to each of a plurality of drive wheels 163. A drive belt 164 frictionally engages the output shaft 162 of the motor 161 and the axel(s) 165 of each of the drive wheels 163. As such, rotation of the output shaft 162 of the motor 161 results in rotation of each of the drive wheels 163.

In various embodiments, the drive assembly 160 can have a manual override that is configured to advance the biological growth plate 10 through manual intervention. The manual override can be configured to rotate the drive wheels 163 when the imaging cassette 120 is not installed in the main body 110 (and thus the drive wheels are not energized by the power supply connector 114). The manual override can be used during maintenance operations, such as when the imaging cassette is being cleaned or to fix operational errors such as if a biological growth plate 10 is out of proper positioning, which may "jam" the system. In the current example, the manual override is a manual rotary knob 169 that is operatively coupled to a drive wheel 163. The manual rotary knob 169 is fixed to a drive axel 165. Manual rotation of the rotary knob 169 rotates the drive axel 165, which causes advancement of the drive belt 164 and, therefore, corresponding rotation of any other drive axels 165 of the drive assembly 160 of the imaging cassette 120. The manual rotary knob 169 can be rotated during cleaning of the drive wheels 163.

The imaging cassette 120 can be configured to frictionally engage the biological growth plate 10 between a drive wheel 163 and a corresponding roller wheel 166 (best visible in FIG. 6). A roller wheel 166 can be configured to be positioned oppositely to each drive wheel 163 relative to the feed channel 127. The roller wheels 166 can have a rotational axis that is parallel to the rotational axis of the drive wheels 163. In some embodiments, a roller wheel 166 is configured to frictionally engage a corresponding drive wheel 163 in the feed channel 127. In some embodiments each roller wheel 166 is configured to apply pressure to an outer radial surface of the corresponding drive wheel 163. Each roller wheel 166 can be biased into a first position where the roller wheel 166 applies pressure to the drive wheel 163. When a biological growth plate 10 is inserted into the feed channel 127, each roller wheel 166 shifts away from the drive wheel 163 to accommodate the thickness of the biological growth plate 10 between each roller wheel 166 and the corresponding drive wheel 163. In such an example, the roller wheels 166 apply pressure to the corresponding drive wheels 163 through the biological growth plate 10. In some alternate embodiments, a space can be defined between a roller wheel 166 and a corresponding drive wheel 163 in the feed channel 127. In such embodiments, the height of the space will generally be less than the thickness of the biological growth plate 10.

A plate clamp 167 is generally coupled to the cassette body 124. The plate clamp 167 can be removably coupled to the cassette body 124 in various embodiments. In the current example, the plate clamp 167 is pivotably coupled to an outer surface of the cassette body 124 at a hinge joint 168. The plate clamp 167 has a clamped position (FIGS. 3 and 5) where the plate clamp 167 and the illumination plate 179 define the feed channel 127 between them. The plate clamp 167 can be configured to cover the drive wheels 163 in the clamped position. The plate clamp 167 can be configured to cover a perimeter region 179a of the illumination plate 179 in the clamped position. The plate clamp 167 has an open position (FIGS. 6 and 7). The open position of the plate clamp 167 can be used to perform maintenance operations on the imaging cassette 120 such as cleaning operations.

The plate clamp 167 can be secured in a clamped position through a variety of approaches such as latches, snap fits, compression fits, and the like. In the currently-depicted example, the plate clamp 167 is secured to the cassette body 124 in the clamped position through a magnetic connection. In particular, a magnet 129 (FIG. 7) can be coupled to the cassette body 124 that is configured to magnetically secure the plate clamp 167 in a clamped position. In such embodiments, the magnetic attraction between the magnet 129 and the plate clamp 167 can be overcome by manually pivoting the plate clamp 167 away from the cassette body 124 about the hinge joint 168.

The plate clamp 167 defines an optical opening 167a that is configured to expose a portion of the illumination plate 179 for light transmission through the plate clamp 167. The optical opening 167a can be a void opening that is free of material. In some embodiments, the optical opening 167a can be defined by a transparent material such as glass, plastic, or the like, that is configured to allow optical communication between the illumination plate 179 and the environment outside of the plate clamp 167. In such embodiments, the transparent material forming the optical opening 167a can help prevent contaminants from settling on the illumination plate 179 from the ambient environment. In various embodiments it can be desirable to configure the plate clamp 167 such that light transmitted from the imaging cavity 115 to the illumination plate 179 does not create a shadow on the illumination plate 179.

In the current example, the roller wheels 166 discussed above are coupled to the plate clamp 167. When the plate clamp 167 is in the clamped position, each roller wheel 166 is positioned to be abutting an outer radial surface of a corresponding drive wheel 163. When the plate clamp 167 is in an open position, each roller wheel 166 is radially aligned with the corresponding drive wheel 163 about the hinge joint 168. In various embodiments, a spring is disposed between each roller wheel 166 and the plate clamp 167 which biases each of the roller wheels 166 towards the corresponding drive wheels 163. As discussed above, the roller wheels 166 can be configured to apply pressure to the corresponding drive wheels 163.

In various embodiments the imaging device 100 is configured to undergo calibration operations such that the settings of the main body 110 and the imaging cassette 120 are optimized as a pair. In implementations where multiple imaging devices 100 are employed, or where spare imaging cassettes are kept in stock, each imaging device 100 can be configured to recognize if an imaging cassette 120 was not calibrated with the main body 110 that the imaging cassette 120 is currently installed in. The imaging device 100 can have a pairing confirmation assembly that is configured to recognize that a main body 110 has not been calibrated with an installed imaging cassette 120.

Figure 8:
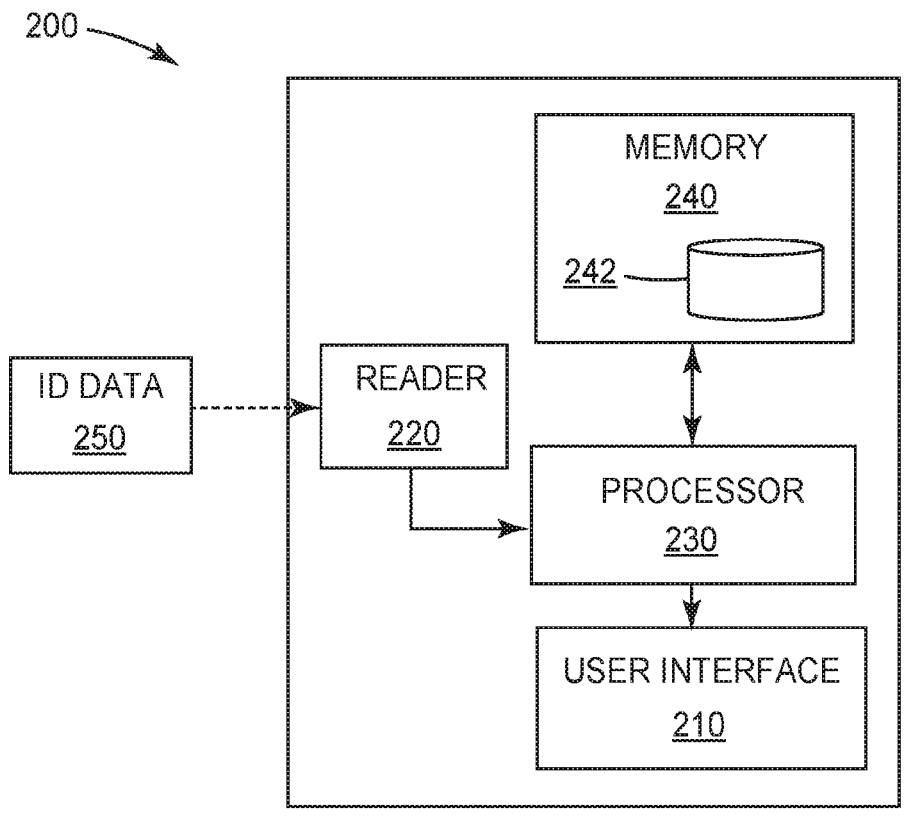
FIG. 8 is a schematic of an example pairing confirmation assembly of an imaging device.

FIG. 8 is a schematic of an example pairing confirmation assembly 200 of an example imaging device. In various embodiments, the pairing confirmation assembly 200 can be configured to provide a user notification upon recognition that the main body (such as the example main body 110 of FIG. 3, for example) has not been calibrated with an installed imaging cassette (such as the example imaging cassette 120 of FIG. 3, for example). The imaging device can have a user interface 210 that is configured to provide the user notification. The user interface 210 can be in data communication with a data reader 220. The user interface 210 can be in data communication with the data reader 220 through a processor 230, for example. In some embodiments the user interface 210 can be a speaker, a screen, a light, or a wireless signal generator that provides the user notification. In some embodiments a warning light can flash to notify a user upon recognition that the main body has not been calibrated with an installed imaging cassette. In some embodiments an audible alarm can issue upon recognition that the main body has not been calibrated with an installed imaging cassette. In some embodiments the imaging device disables device operation upon recognition that the main body has not been calibrated with an installed imaging cassette.

In some embodiments, the imaging device has a memory 240 that is configured to store configuration data 242 identifying the pairing and calibration of a particular imaging cassette with a particular main body. The configuration data 242 can include an identification of the imaging cassette such as a serial number, for example. The configuration data 242 can include an identification of the main body, such as a serial number. Configuration data 242 can also include operational parameters resulting from calibration of the imaging cassette with the main body. In some embodiments, configuration data 242 can include a recorded date of calibration of the imaging cassette with the main body. The memory 240 can be a component of the main body. However, in other embodiments, the memory can be a component of the imaging cassette. In some embodiments, each of the main body and the imaging cassette can have memory configured to store the configuration data.

The data reader 220 is configured to read a portion of the configuration data such as identification data of the main body. The data reader 220 can be configured to read identification data 250 of the imaging cassette. In some embodiments the data reader 220 can include an optical scanner such as a barcode scanner. In some embodiment the data reader 220 can include a radio frequency identification (RFID) sensor that is configured to read an RFID chip of the imaging cassette or the main body. Such an RFID chip can provide data representing a serial number of the imaging cassette or the main body. Other types of data readers 220 can also be used. In some embodiments the main body has the data reader 220 that is configured to read identification data 250 defined by the imaging cassette. In some embodiments imaging cassette has the data reader 220 that is configured to read identification data 250 defined by the main body.

Upon installation of an imaging cassette in a main body, the data reader 220 is configured to read the identification data 250. The pairing confirmation assembly 200, and particularly a processor 230 of the pairing confirmation assembly 200, is configured to compare the read identification data 250 to the stored configuration data 242 in the memory 240. If the read identification data 250 matches the stored configuration data 242, then the imaging device can be used for imaging. If the read identification data 250 does not match the stored configuration data 242, then the imaging device can provide a user notification that the data 250, 242 does not match. In some embodiments, the imaging device can provide a user notification that the main body has not been calibrated with an installed imaging cassette through the user interface 210. In some embodiments, no notification is provided through a user interface 210. As such, a user interface 210 may be omitted. In such embodiments, the imaging device may be configured to obstruct device operation by the user until configuration operations are completed. In some embodiments incorporating a user interface 210, the imaging device prompts the user to initiate configuration operations.

In some embodiments, the main body is configured to store configuration data 242 associated with each of multiple imaging cassettes that have each been calibrated with the main body. In such embodiments, the main body can be configured to update system settings to match the specific configuration data associated with a currently installed imaging cassette if that imaging cassette was previously calibrated with the main body. Upon installation of a second imaging cassette, the main body can be configured to update system settings to match the specific configuration data with the second imaging cassette.

EXEMPLARY EMBODIMENTS

Embodiment 1. A removable imaging cassette comprising:
an illumination plate configured to transmit light;
a cassette body defining an outer surface and a cassette cavity within the outer surface, wherein the outer surface surrounds the illumination plate and the cassette cavity abuts the illumination plate;
a light source disposed in the cassette cavity; and
mating electrical contacts extending through the outer surface of the cassette body, wherein the mating electrical contacts are operably coupled to the light source.

Embodiment 2. The removable imaging cassette of any one of embodiments 1 and 3-8, further comprising:
a drive wheel rotatably coupled to the outer surface of the cassette body adjacent the illumination plate; and
a motor operably coupled to the drive wheel, wherein the motor is disposed in the cassette cavity and wherein the mating electrical contacts are operably coupled to the motor.

Embodiment 3. The removable imaging cassette of any one of embodiments 1-2 and 4-8, further comprising a manual rotary knob operably coupled to the drive wheel.

Embodiment 4. The removable imaging cassette of any one of embodiments 1-3 and 5-8, further comprising a plate clamp coupled to the cassette body, and a roller wheel rotatably coupled to the plate clamp, wherein the roller wheel is configured to align with the drive wheel.

Embodiment 5. The removable imaging cassette of any one of embodiments 1-4 and 6-8, wherein the plate clamp is pivotably coupled to the outer surface of the cassette body.

Embodiment 6. The removable imaging cassette of any one of embodiments 1-5 and 7-8, further comprising a manually engageable handle coupled to the cassette body.

Embodiment 7. The removable imaging cassette of any one of embodiments 1-6 and 8, wherein the cassette body defines a media slot extending from the outer surface to the illumination plate.

Embodiment 8. The removable imaging cassette of any one of embodiments 1-7, wherein the cassette cavity is isolated from an ambient environment.

Embodiment 9. An imaging device comprising:
a main body having an outer shell, the main body defining a main cavity and a cassette receptacle extending through the outer shell to the main cavity;
source electrical contacts coupled to the outer shell, wherein the source electrical contacts are exposed in the main cavity;
a power supply connector configured to couple to a power source, wherein the power supply connector is in electrical communication with the source electrical contacts; and
an imaging cassette removably installed in the cassette receptacle, the imaging cassette comprising:
an illumination plate configured to transmit light;
a cassette body defining an outer surface and a cassette cavity within the outer surface, wherein the outer surface surrounds the illumination plate and the cassette cavity abuts the illumination plate; and
mating electrical contacts configured to (1) electrically mate with the source electrical contacts when the imaging cassette is installed in the cassette receptacle, and (2) electrically disconnect from the source electrical contacts when the imaging cassette is removed from the cassette receptacle.

Embodiment 10. The imaging device of any one of embodiments 9 and 11-21, wherein the illumination plate is configured to receive a biological growth plate.

Embodiment 11. The imaging device of any one of embodiments 9-10 and 12-21, further comprising a light source disposed in the cassette cavity, wherein the mating electrical contacts are operably coupled to the light source.

Embodiment 12. The imaging device of any one of embodiments 9-11 and 13-21, further comprising a transparent barrier mounted to the main body in the main cavity between the cassette receptacle and an imaging cavity.

Embodiment 13. The imaging device of any one of embodiments 9-12 and 14-21, further comprising a pairing confirmation assembly comprising a reader and an identifier, wherein the reader is configured to read the identifier and the pairing confirmation assembly is configured to compare the identifier to stored configuration data.

Embodiment 14. The imaging device of any one of embodiments 9-13 and 15-21, wherein the main body comprises a user interface in data communication with the reader, wherein the user interface is configured to notify a user that the identifier does not match the stored configuration data.

Embodiment 15. The imaging device of any one of embodiments 9-14 and 16-21, further comprising:

a drive wheel rotatably coupled to the cassette body adjacent the illumination plate; and a motor operably coupled to the drive wheel, wherein the motor is disposed in the cassette cavity and wherein the mating electrical contacts are operably coupled to the motor.

Embodiment 16. The imaging device of any one of embodiments 9-15 and 17-21, further comprising a manual rotary knob operably coupled to the drive wheel.

Embodiment 17. The imaging device of any one of embodiments 9-16 and 18-21, further comprising a plate clamp coupled to the cassette body, and a roller wheel rotatably coupled to the plate clamp, wherein the roller wheel is configured to align with the drive wheel.

Embodiment 18. The imaging device of any one of embodiments 9-17 and 19-21, wherein the plate clamp is pivotably coupled to the outer surface of the cassette body.

Embodiment 19. The imaging device of any one of embodiments 9-18 and 20-21, further comprising a manually engageable handle coupled to the cassette body.

Embodiment 20. The imaging device of any one of embodiments 9-19 and 21, wherein the cassette body defines a media slot extending from the outer surface to the illumination plate.

Embodiment 21. The imaging device of any one of embodiments 9-20, wherein the cassette cavity is isolated from an ambient environment.

It should also be noted that, as used in this specification and the appended claims, the phrase "configured" describes a system, apparatus, or other structure that is constructed to perform a particular task or adopt a particular configuration. The word "configured" can be used interchangeably with similar words such as "arranged", "constructed", "manufactured", and the like.

All publications and patent applications in this specification are indicative of the level of ordinary skill in the art to which this technology pertains. All publications and patent applications are herein incorporated by reference to the same extent as if each individual publication or patent application was specifically and individually indicated by reference. In the event that any inconsistency exists between the disclosure of the present application and the disclosure(s) of any document incorporated herein by reference, the disclosure of the present application shall govern.

This application is intended to cover adaptations or variations of the present subject matter. It is to be understood that the above description is intended to be illustrative, and not restrictive, and the claims are not limited to the illustrative embodiments as set forth herein.

What is claimed is:

1. A removable imaging cassette comprising:

an illumination plate configured to transmit light;

a cassette body defining an outer surface and a cassette cavity within the outer surface, wherein the outer surface surrounds the illumination plate and the cassette cavity abuts the illumination plate;

a light source disposed in the cassette cavity; and mating electrical contacts extending through the outer surface of the cassette body, wherein the mating electrical contacts are operably coupled to the light source.

2. The removable imaging cassette of claim 1, further comprising:

a drive wheel rotatably coupled to the outer surface of the cassette body adjacent the illumination plate; and a motor operably coupled to the drive wheel, wherein the motor is disposed in the cassette cavity and wherein the mating electrical contacts are operably coupled to the motor.

3. The removable imaging cassette of claim 1, further comprising a manual rotary knob operably coupled to the drive wheel.

4. The removable imaging cassette of claim 1, further comprising a plate clamp coupled to the cassette body, and a roller wheel rotatably coupled to the plate clamp, wherein the roller wheel is configured to align with the drive wheel.

5. The removable imaging cassette of claim 1, wherein the plate clamp is pivotably coupled to the outer surface of the cassette body.

6. The removable imaging cassette of claim 1, further comprising a manually engageable handle coupled to the cassette body.

7. The removable imaging cassette of claim 1, wherein the cassette body defines a media slot extending from the outer surface to the illumination plate.

8. The removable imaging cassette of claim 1, wherein the cassette cavity is isolated from an ambient environment.

9. An imaging device comprising:

a main body having an outer shell, the main body defining a main cavity and a cassette receptacle extending through the outer shell to the main cavity;

source electrical contacts coupled to the outer shell, wherein the source electrical contacts are exposed in the main cavity;

a power supply connector configured to couple to a power source, wherein the power supply connector is in electrical communication with the source electrical contacts; and an imaging cassette removably installed in the cassette receptacle, the imaging cassette comprising:

an illumination plate configured to transmit light;

a cassette body defining an outer surface and a cassette cavity within the outer surface, wherein the outer surface surrounds the illumination plate and the cassette cavity abuts the illumination plate; and mating electrical contacts configured to (1) electrically mate with the source electrical contacts when the imaging cassette is installed in the cassette receptacle, and (2) electrically disconnect from the source electrical contacts when the imaging cassette is removed from the cassette receptacle.

10. The imaging device of claim 9, wherein the illumination plate is configured to receive a biological growth plate.

11. The imaging device of claim 9, further comprising a light source disposed in the cassette cavity, wherein the mating electrical contacts are operably coupled to the light source.

12. The imaging device of claim 9, further comprising a transparent barrier mounted to the main body in the main cavity between the cassette receptacle and an imaging cavity.

13. The imaging device of claim 9, further comprising a pairing confirmation assembly comprising a reader and an identifier, wherein the reader is configured to read the identifier and the pairing confirmation assembly is configured to compare the identifier to stored configuration data.

14. The imaging device of claim 9, wherein the main body comprises a user interface in data communication with the reader, wherein the user interface is configured to notify a user that the identifier does not match the stored configuration data.

15. The imaging device of claim 9, further comprising:
    a drive wheel rotatably coupled to the cassette body adjacent the illumination plate; and a motor operably coupled to the drive wheel, wherein the motor is disposed in the cassette cavity and wherein the mating electrical contacts are operably coupled to the motor.

16. The imaging device of claim 9, further comprising a manual rotary knob operably coupled to the drive wheel.

17. The imaging device of claim 15, further comprising a plate clamp coupled to the cassette body, and a roller wheel rotatably coupled to the plate clamp, wherein the roller wheel is configured to align with the drive wheel.

18. The imaging device of claim 17, wherein the plate clamp is pivotably coupled to the outer surface of the cassette body.

19. The imaging device of claim 9, further comprising a manually engageable handle coupled to the cassette body.

20. The imaging device of claim 9, wherein the cassette body defines a media slot extending from the outer surface to the illumination plate.

21. The imaging device of claim 9, wherein the cassette cavity is isolated from an ambient environment.

* * * * *